United States Patent [19]

Larsson

[11] Patent Number: 5,007,899
[45] Date of Patent: Apr. 16, 1991

[54] DRIVE UNIT ADAPTED FOR USE WITH MANUAL PISTON PUMP

[75] Inventor: Karl O. A. H. Larsson, Schweiz, Switzerland

[73] Assignee: ISG/AG, Zug, Switzerland

[21] Appl. No.: 162,056

[22] Filed: Feb. 29, 1988

[51] Int. Cl.⁵ .............................................. A61M 1/06
[52] U.S. Cl. ..................... 604/74; 604/120; 604/154
[58] Field of Search .................... 604/73–76, 604/119–121, 151, 152, 315, 346; 119/14.32, 14.33, 14.53

[56] References Cited

U.S. PATENT DOCUMENTS

| | | | |
|---|---|---|---|
| 1,509,226 | 9/1924 | Brown | 604/74 |
| 1,644,257 | 10/1927 | Lasker | 604/120 |
| 1,966,498 | 7/1934 | Gross | 604/152 |
| 2,419,795 | 4/1947 | Saunders | 604/74 |
| 4,067,332 | 1/1978 | O'Leary | 604/152 |
| 4,583,970 | 4/1986 | Kirchner | 604/74 |
| 4,759,747 | 7/1988 | Aida et al. | 604/74 |

FOREIGN PATENT DOCUMENTS

| | | | |
|---|---|---|---|
| 0251810 | 9/1948 | Switzerland | 604/74 |
| 0271857 | 11/1927 | United Kingdom | 604/74 |

OTHER PUBLICATIONS

Lawrence, "Breastfeeding", pp. 467–469 (4-16-86).

Primary Examiner—C. Fred Rosenbaum
Assistant Examiner—Mario Costantino
Attorney, Agent, or Firm—Willian Brinks Olds Hofer Gilson & Lione

[57] ABSTRACT

An improved breast pump assembly, including a manually operable breast pump that can be used in a manual mode by hand-driving the breast pump, provides a motor drive unit which is adapted to receive and hold the manually operable piston pump of the breast pump, with a pump drive for reciprocating the piston rod of the piston pump in substantially the same stroke as would occur in optimum manual driving of the breast pump.

13 Claims, 4 Drawing Sheets

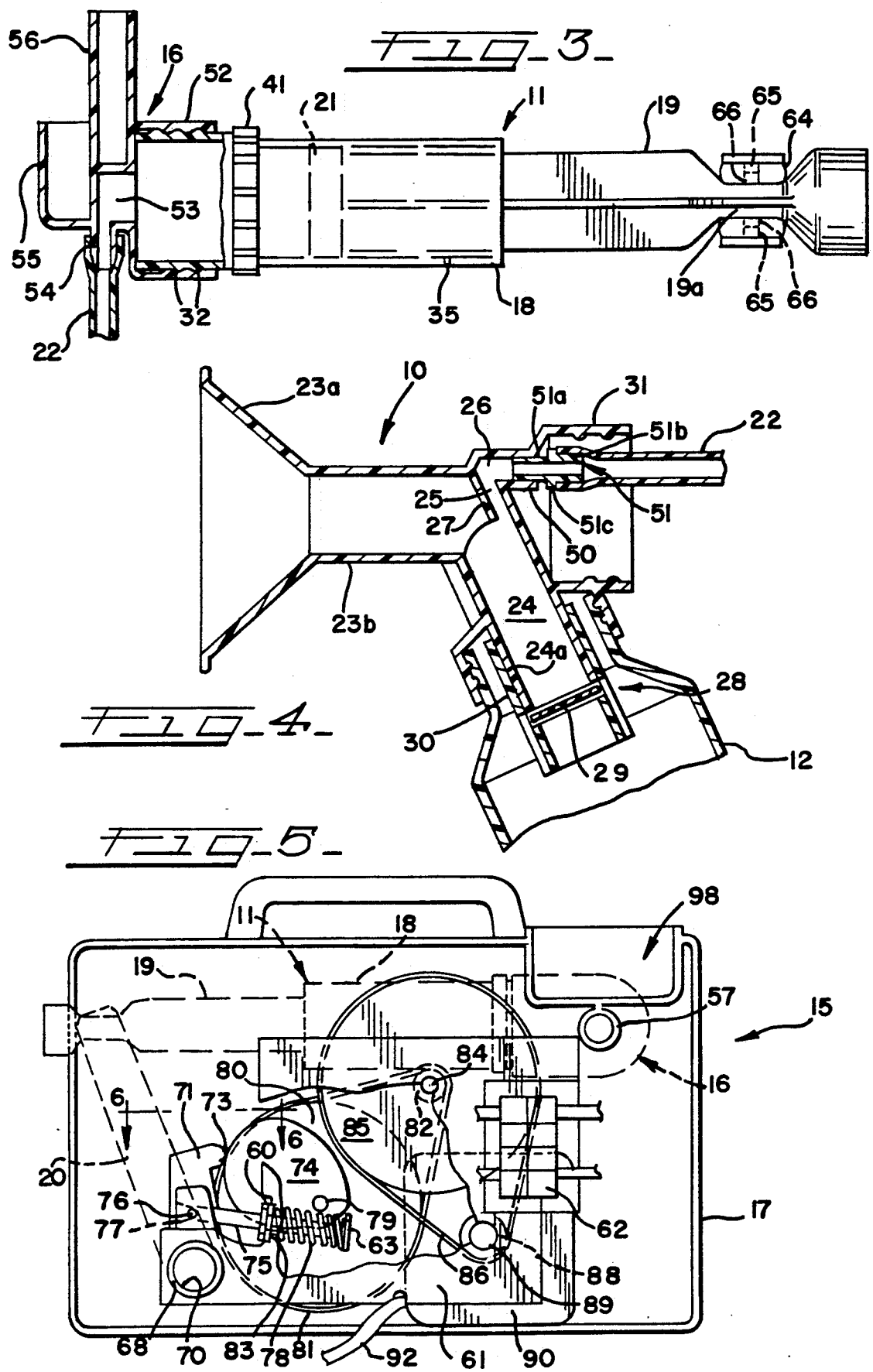

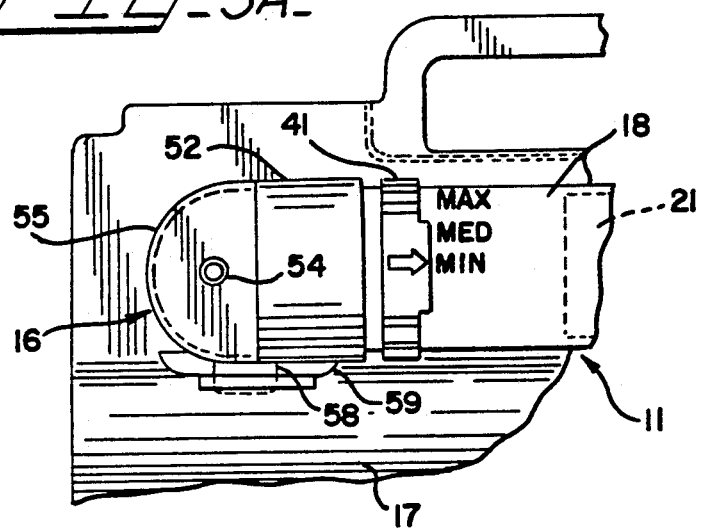
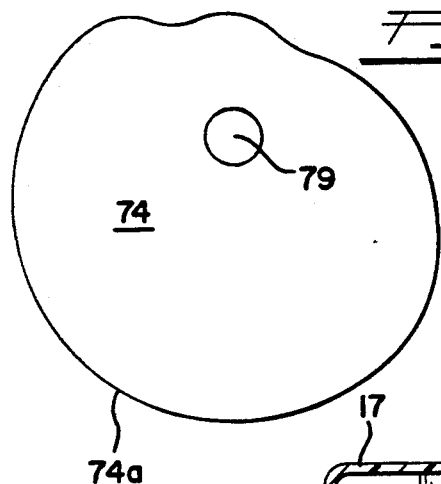
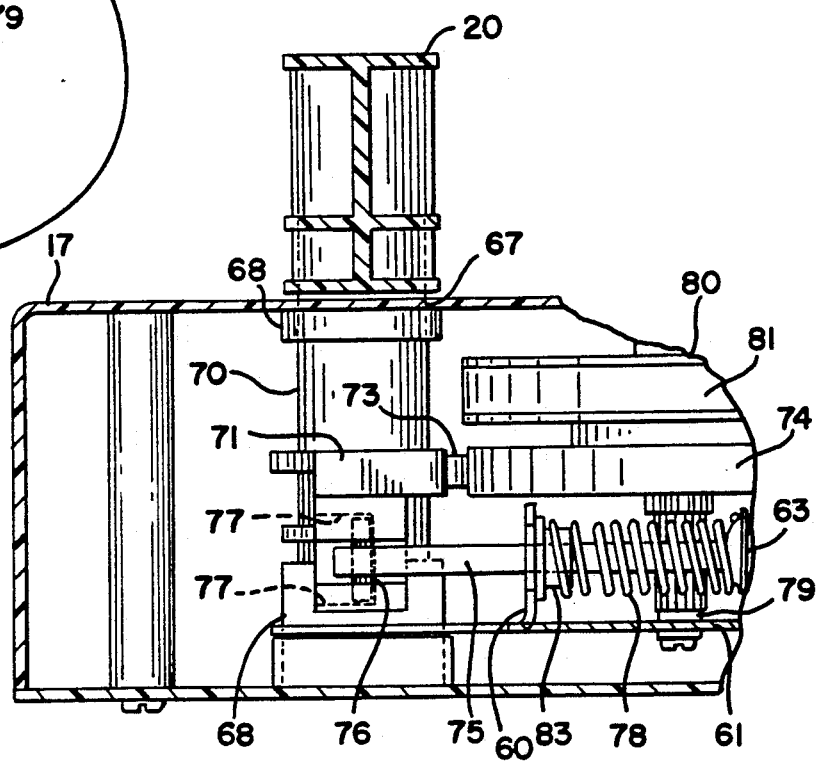

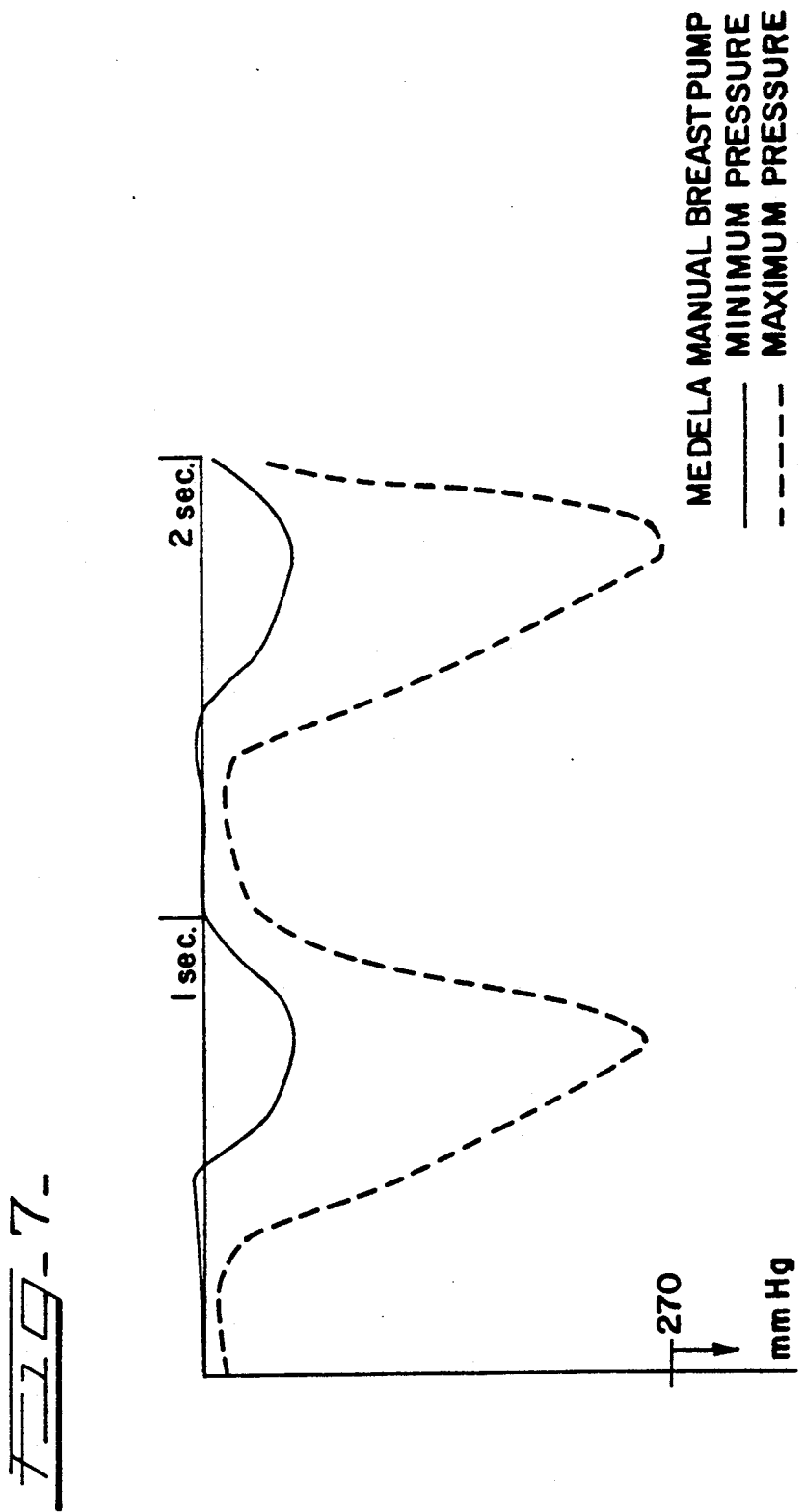

DRIVE UNIT ADAPTED FOR USE WITH MANUAL PISTON PUMP

FIELD OF THE INVENTION

This invention relates generally to breastmilk pumps, and particularly to breast pumps for use in the expression of mothers' milk which include a manually driven pump mechanism, such as a piston pump.

BACKGROUND OF THE INVENTION

Pumps used to extract or express, mothers milk are well known. Breastmilk pumps are adapted to massage the breast to relieve it of its contents of milk, such as for storage in a container for later use by an infant.

Breast pumps typically come in two types: those that are driven off of a motor, and those that are driven by hand, that is, manual pumps (although Applicant's assignee, Medela Inc., markets a MANUALECTRIC pump which is capable of use either as a manual pump or can be adapted for use with a motor drive. See Applicant s co-pending application U.S. Ser. No. 07/053 055 filed May 22 1987). Typically, these breast pumps include a funnel-shaped rigid hood which is emplaceable over the nipple and a substantial portion of the breast. A reduced pressure or vacuum is then intermittently generated within the hood to create a suction which draws the nipple and adjacent breast further into the narrower portion of the hood. This pulling action both massages and constricts the breast in a manner reminiscent of suckling, resulting in the expression of milk into the funnel opening of the hood. The milk then typically flows into a collecting chamber or container for storage for later use or disposal.

The means generally used for generating the intermittent suction within the hood in a manually driven pump is a compressible bulb or preferably a pneumatic piston pump. The latter commonly would include a piston cylinder that is connected to the hood, with a piston mounted for reciprocating movement within the piston cylinder, such as under the driving action of a hand-driven piston rod connected at one end to the piston, with the other end extending out of the rear of the piston cylinder. Further details regarding a breast pump with such a manually driven piston pump can be gleaned from the aforementioned U.S. patent application Ser. No. 07/053,055.

SUMMARY OF THE INVENTION

The manually driven breast pump described above has many advantages, such as its relatively compact nature and its operability without an electric power source, enabling it to be readily transported and used anywhere, There are times, however, where transportation of the breast pump and power requirements are not significant factors, such as in the home or in a hospital environment, for two examples. In those instances, it can be desirable to have a motor driven breast pump to dispense with the need to manually drive the breast pump. It is accordingly a primary objective of the present invention to provide an improved breast pump assembly which includes such a manually operable breast pump, with a motor drive unit adapted to mechanically drive the otherwise hand-drivable pump to effect the expression of mothers' milk.

More particularly, the present invention comprises an improved breast pump assembly including a manually operable breast pump having a hand-drivable piston which is received for reciprocating movement in a piston cylinder. As previously noted, the reciprocating action of the piston generates a periodic suction within the breast-hood emplaced over a breast to thereby express milk. A motor drive unit is adapted to receive and hold the manually operable breast pump. The drive unit includes a motor and related driving mechanism for driving the piston pump.

In the embodiment of the invention described herein, the piston pump portion of the breast pump assembly is attached to the casing of the drive unit with an adaptor that fits over the forward end of the piston cylinder. The piston rod is received within a U-shaped resilient gripping member, or clamp, on one end of an arm. The other end of the arm is pivotably attached to the casing, and is connected to a mechanism which cyclically turns the arm through an arc to thereby effect the reciprocating movement of the piston rod as if it were being driven by hand. An electric motor is connected to the arm turning mechanism to drive the latter.

The motor drive unit is constructed to provide a suction stroke of the piston pump which substantially reproduces the same stroke as optimum manual driving of the breast pump would do. Such an optimum stroke is presently considered to be a suction generated in the range of about a maximum of at least 100 to preferably about 250 mmHg, over a stroke rate of about 50-60 cycles per minute.

The present invention achieves the indicated objective of providing a motor drive unit for use with an otherwise manually drivable piston pump of a breast pump. Virtually no adaptation of the manual breast pump is required, other than attaching its piston pump to the motor drive unit adaptor. The inventive breast pump assembly can be readily interchanged between manual and motor driven modes. Other benefits include the ability to provide a kit to a number of users in a hospital, for example, with a manual pump supplied to each user. A single motor drive unit can then be used with a number of users without any unhygienic risks.

In this regard, the hygienic aspect of the invention can be further highlighted. Prior art motor driven pumps used only by even a single user face a problem of bacteriologic contamination. Overflow protection is necessary to prevent milk from entering the pump air line. Even so, contaminated air can still enter the pump air line. This risk of contamination to the motor air line is completely eliminated by the present invention, since the motor drive mechanism has no internal air line to be contaminated —it simply mechanically drives the manual piston pump, and no fluid passes between the breast pump and the drive mechanism.

Further details concerning the invention and its advantages can be obtained from the following detailed description of an embodiment of the invention, taken in conjunction with the accompanying drawings, in which:

BRIEF DESCRIPTION OF THE DRAWINGS

FIG. 3 is an enlarged sectional view taken along line 3—3 of FIG. 1 detailing the attachment of the piston pump to the motor drive unit;

FIG. 3A is an elevational view of the attachment of the forward end of the piston pump to the motor drive unit;

FIG. 4 is an enlarged sectional view taken along line 4—4 of FIG. 1 detailing the breast-hood assembly;

FIG. 5 is a view taken through the back of the motor drive unit (relative to FIG. 1) partially broken away for detail of the drive mechanism;

FIG. 5A is a full-scale elevational view of the driving cam;

FIG. 6 is an enlarged view taken along line 6—6 of FIG. 5; and

FIg. 7 is a chart showing the preferred optimum cycle for the pump.

DETAILED DESCRIPTION OF AN EMBODIMENT OF THE INVENTION

General Organization And Operation

Figure 2:
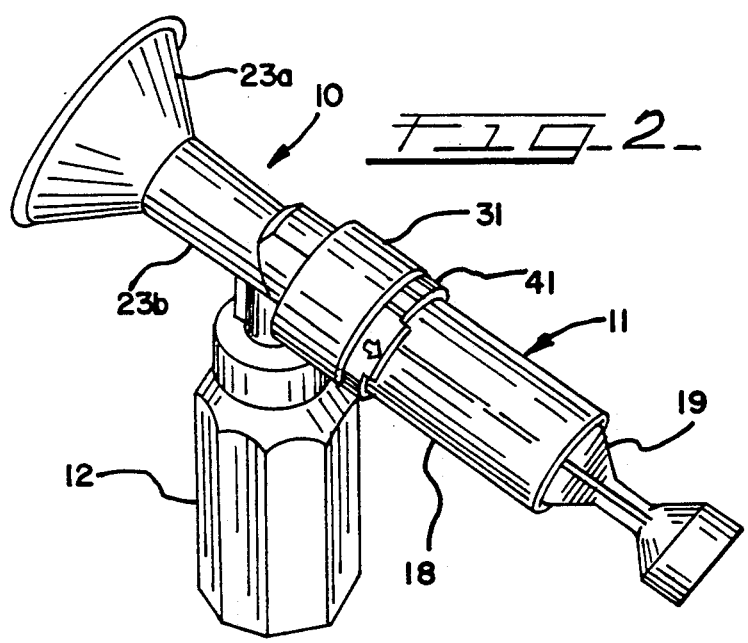
FIG. 2 shows the breast pump of FIG. 1 set up for manual operation of the breast pump.

The improved breast pump assembly illustrated herein includes two principal components. One is a manually operable breast pump, which is shown set up for manual operation in FIG. 2. The breast pump has a breast-hood assembly 10 and a hand-drivable piston pump 11 which connects to the breast-hood assembly in a manner which will be described in more detail hereafter. A container for the collection of breast milk, such as a bottle 12 is attached to the lower portion of the breast-hood assembly 10.

Figure 1:
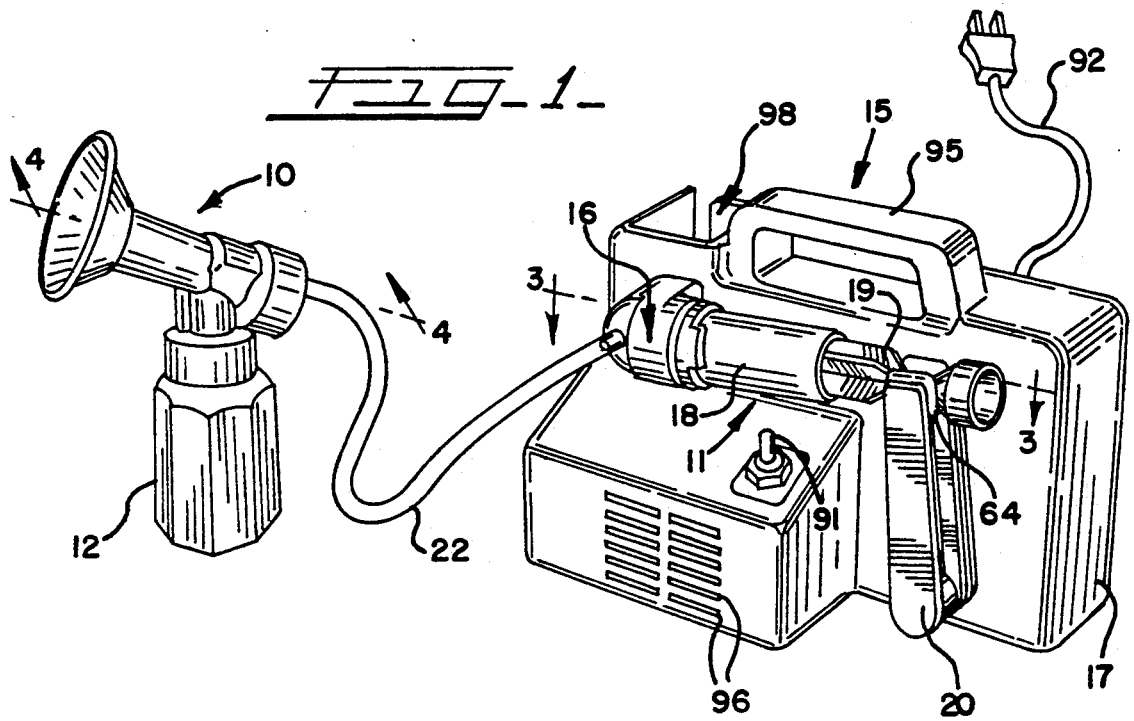
FIG. 1 is a perspective view showing an improved breast pump assembly made in accordance with the present invention.

The other principal component of the improved breast pump assembly is the motor drive unit 15 (e.g., FIGS. 1 and 5). The motor drive unit 15 is adapted to receive and hold the piston pump 11 when detached from the breast hood assembly 10, and to mechanically drive the piston pump 11. To this end, the motor drive unit 15 has an adaptor 16 which is attachable to a casing 17 of the drive unit (FIGS. 1. 3 and 3A). A piston cylinder 18 of the piston pump 11 is received in the adaptor 16. Piston rod 19 of the piston pump 11 is releasably held at one end of an arm 20, which is mounted at its other end to the casing 17.

A motor driven mechanism is provided for cyclically turning the arm 20 through an arc to effect the reciprocating movement of the piston rod 19 and a piston 21 in a manner substantially similar to that of manually driving the piston rod 19. This drive mechanism will be described in more detail hereinafter, as will other aspects of this embodiment. A length of tubing 22 interconnects the adaptor 16 with the breast hood assembly 10 to communicate the negative pressure generated in the rearward stroke of the piston pump 11 for suction in the breast-hood assembly 10.

The Manual Breast Pump

The manually operable breast pump shown herein, and generally comprised of hood-assembly 10 and piston pump 11, is substantially the same as that shown in the aforementioned co-pending U.S. patent application Ser. No. 07/053,055 which is incorporated herein by reference. Briefly, that breast pump has a hood body or hood member having two ends. The first end 23a has a substantially wide cross-section (diameter). and is funnel-shaped. A second end 23b of the hood member constitutes a generally cylindrical extension of the funnel, and has a cross-section substantially narrower than the cross-section of the end 23a. The second end 23b communicates with a collecting or catch chamber 24 defined by a tubular extension 24a, and with a vacuum passage 25.

The vacuum passage 25 also communicates with a vacuum line 26, which in this embodiment is defined by a short tubular extension or collar 50. A depending separation wall 27 forms a baffle between the end of the funnel portion 23b and the vacuum line 26, with the bottom of the separation wall 27 below the level of the vacuum line 26. Milk expressed into the hood member is thus blocked by the separation wall 27 from thereby entering the vacuum line 26.

At the lower portion of the collecting chamber 24 is a valve mechanism 28. The valve mechanism 28 uses a disk-member 29 as the valving member, with the disk 29 captured within a tubular-shape valve housing 30. When the breast pump is operated, the disk 29 is caused to move upwardly under vacuum where it contacts and seats against the bottom edge or lip of the tubular extension 24a forming the chamber 24, thus closing the collecting chamber 24. When the vacuum is released, the disk 29 drops free from the foregoing seat allowing milk collected in the collecting chamber 24 to flow downwardly into the container 12. The valve mechanism 28 is attached to the outside of the tubular extension 24a via a snug interference attachment.

The manually driven piston pump 11 (FIGS. 2 and 3) is connected to the breast-hood assembly 10 by connecting sleeve 31 (FIG. 4). Connecting sleeve 31 is internally screw-threaded, with the threads matched to the screw threads 32 formed on the forward end of the piston cylinder 18 (FIG. 3). The forward end of the piston cylinder 18 butts against a shoulder formed on the interior of the connecting sleeve 31 in a substantially air-tight fit. An aperture 35 is formed in the wall of the piston cylinder 18 at a point which corresponds to what is presently considered to be the maximum desired vacuum pressure to be reached on an average stroke of the piston pump 11. Once the head of the piston 21 passes beyond this aperture 35 in its vacuum-inducing stroke, the vacuum produced is automatically released.

An adjustment mechanism for varying the amount of vacuum generated during pumping is also provided. This is represented in the illustrations by a ring 41 carried on the piston cylinder 18 adjacent its forward end which overlies a pair of holes (not shown) through the cylinder 18. An interior chamber or channel (also not shown) is formed in the inside of the ring 41. The channel formed in the ring 41 has one or more openings that are opened to atmosphere. The ring 41 is preferably made out of a flexible or semi-flexible rubber-like material that enables a good seal to be maintained between the ring 41 and the piston cylinder 18.

The ring 41 is rotated on the piston cylinder 18 to positions indicated as "Maximum," "Medium", and "Minimum" vacuum (see FIG. 3A). The range of vacuum is dependent upon the hole or holes in the cylinder 18 which fall within the area of the channel in the ring 41 when the ring is rotated. Again further detail concerning the construction and operation of the vacuum adjusting ring 41, as well as of the breast pump in general, can be obtained from co-pending patent application Serial No. 07/053,055.

An adaptation to the breast pump described in the aforementioned patent application Ser. No. 07/053,055 takes the form herein of a tubular extension or collar 50 formed in the upper part of the vacuum passage 25. A tubular connector 51 has one end 51a that is received in the collar 50 in a snug fit. The other end 51b of the connector fits within one end of the tubing 22 in a snug fit. There is a slight radially extending shoulder 51c formed on the connector 51 which serves as an end stop for the tubing 22. It may be noted that this arrangement for connecting the tubing 22 to the vacuum passage 25 has advantages over the type of adaptor used for an electric pump described in U.S. Ser. No. 07/053,055, in that the connection of the tubing 22 is directly into the vacuum passage 25. While this direct connection is considered of increased advantage, the present invention can nevertheless be used successfully with the type of pump adaptor shown in U.S. Ser. No. 07/053,055, without any need to modify the breast-hood assembly shown therein.

The Motor Drive Unit

Referring to FIG. 3, it is of course clear that there is no modification required whatever to the piston pump 11 shown in U.S. Ser. No. 07/053,055 for use in the present breast pump assembly. Piston cylinder 18 has its forward end screw threaded (at 32) for attachment to the connecting sleeve 31 of the hood assembly 10 for use in the manually driven mode. When it is desired to mechanically drive the piston pump 11, the adaptor 16 is used.

Adaptor 16 has cap portion 52 which is match-threaded for substantially airtight attachment to the piston cylinder 18. Inside of the cap 52 (FIG. 3) is a small chamber 53 which communicates with the interior of the cap 52, and therefore also with the piston chamber. Extending off of the chamber 53 is a nipple-like outlet 54. Outlet 54 is sized to be received within the other end of the tubing 22.

The adaptor 16 has a rounded-off sidewall 55 which extends from the cap 52, and which gives the adaptor 16 a more pleasing appearance. A hollow post 56 is received within a post hole 57 (see FIG. 5) to mount the adaptor to the casing 17. The adaptor 16 is additionally fixed in place on the casing 17 through use of a flange 58 (FIG. 3A) extending from sidewall 55. With the post 56 fully inserted within the post hole 57, adaptor 16 can be rotated clockwise so that a portion of flange 58 slides into an enlarged slot 59 formed in the casing 17. Post 56 is secured in the post hole 57 in this manner for a firm connection of the adaptor 16 to the casing 17.

With particular reference to FIGS. 1 and 3, piston rod 19 is received within a resilient U-shaped silicone grip or clamp 64 which is sized smaller than a necked-in portion 19a of piston rod 19. The piston rod necked-in portion 19a is forced into the resilient grip 64, which in turn tightly holds the piston rod to the arm 20. The grip 64 is pivotally attached to the U-shaped end of the arm (FIG. 3) through the use of a pair of opposed bosses 65 that are received in corresponding holes 66 formed in opposed lateral sides of the grip 64.

The arm 20 has an I-beam type construction for strength and light weight. The lower end of the arm 20 is pivotally attached to the casing 17 via an elongated post 70 that extends through a hole 67 in the casing 17. The post 70 is fixed to the arm 20, and is rotatably mounted in a pair of tubular supports 68 formed on the casing floor. Also fixedly mounted to the post 70 is an interior arm 71.

Interior arm 71 has a hard smooth bearing 73 mounted at its free upper end to bear against the outside edge of eccentric or cam 74. A metal rod 75 is attached at one end to the arm 71 via a pin 76 inserted radially through a hole in the rod 75, and received in a pair of opposed pin end receptacles 77 (V-shaped slots).

A spring 78 is mounted concentric with rod 75. One end of the spring 78 is received on a button 83, which in turn fits within an opening provided in an inwardly extending flange 60. Flange 60 is turned from a metal mounting plate 61. Mounting plate 61 also carries the electrical connections for the drive mechanism shown schematically at 62. The other end of the spring 78 bears against a disk 63 fixed to the free end of the rod 75. The spring 78 is loaded in this fashion to bias the arm 71 into constant engagement with the side edge of cam 74 (via bearing surface 73).

As best seen in FIG. 5A, cam 74 is eccentric, as previously noted, and has an edge surface 74a designed to impart movement to interior arm 71 to drive arm 20 in the desired pumping cycle. Cam 74 is mounted to the shaft 79 of a sprocket 80 (FIG. 5). Cam 74 thus turns with the sprocket 80. Sprocket 80 is turned by a toothed drived belt 81 which is driven off of a reducing gear 82 mounted on a drive shaft 84. A wheel 85 is also mounted on drive shaft 84, and has a smooth surface on which smooth drive belt 86 is received.

Drive belt 86 is in turn connected to a smooth small cylinder 88 which is fixed to drive a shaft 89 of a suitable drive motor 90. Motor 90 is turned on and off with toggle switch 91. A power cord 92 connects the motor to a power source. A suitable drive motor has been found by applicant to be a 12 v. dc. type motor for a battery driven power source or an a.c. type motor for a motor operated off of residential current (110 v).

The particular type of motor for driving the arm 20 is not considered to be of any particular significance in and of itself to the operation of the invention, so long as it is sufficient for the foregoing purposes. Further detail concerning the size of elements, mounting, materials, electrical connections and the like for the drive mechanism have also been omitted as falling well within the skill of those in the art, particularly in view of additional detail shown in the drawings.

The drive mechanism should serve to reciprocate the piston pump 11 in a manner substantially the same as what is considered to be the optimum manual pumping cycle. Such an optimum cycle is considered at present to be a suction stroke which generates a maximum suction in the breast-hood in a range of about 250 mmHg at the top end, to no less then about 100 mmHg at the lower end. More suction than about 250 mmHg could result in discomfort or injury, and less than about 100 mmHg may not effect efficient milk expression. A suction stroke of approximately 50–60 cycles/min. is also considered desirable with 50 cycles/min. presently preferred.

The preferred optimum cycle is illustrate in FIG. 7. It is designed to duplicate the same suction pattern as a suckling baby—a regular, rhythmic series of cycles each consisting of suction, release and relaxation. The surface 74a of cam 74 is designed to reproduce this optimum cycle in driving the arm 71. The mechanism used to obtain this optimum stroke and suction may obviously vary with the type of piston pump and hood assembly being utilized, with the mechanism described herein being particularly adapted for use with the piston pump and breast hood described.

Casing 17 encloses the drive mechanism and serves as a mount for the various elements of the drive mechanism. The casing 17 further includes a handy carrying handle 95. Vents 96 provide air inlets for a cooling fan (not shown) associated with the motor 90. A well 98 is also formed in the top of the casing 17, within which the bottle 12 can be temporarily held for convenience.

Thus, while the invention has been described with reference to a particular embodiment, those having skill in the art will recognize modifications of elements and structure which may facilitate the application of the invention, but which still will fall within the scope of the invention.

What is claimed is:

1. An improved breast pump assembly including a hand-held manually operable breast pump having a hand-drivable piston pump with a piston rod specifically adapted to be grasped to drive a piston received for reciprocating movement within a chamber of a piston cylinder to generate, in use, a periodic suction within a breast-hood emplaced on a breast to effect the expression of mother's milk, wherein the improvement comprises:

a motor drive unit having means for releasably receiving and holding the hand-drivable piston pump, said drive unit further having means for driving the piston rod for reciprocating movement of the piston in the piston chamber.

2. The improved breast pump assembly of claim 1 wherein the piston cylinder has a forward and a rearward end, the forward end being connectable to a breast-hood assembly including the breast hood to generate suction in the breast hood through movement of the piston in the piston cylinder, the piston having a piston rod connected thereto, which piston rod extends out of the rearward end of the piston cylinder.

said motor drive unit including a casing means mounted on said casing for releasably receiving and holding the forward end of the piston cylinder, an arm having first and second ends, said first arm end having means thereon for releasable receiving and holding the piston rod, said second arm end being connected to means for turning said arm through an arc in a reciprocating fashion to effect reciprocating movement of the piston rod to drive the piston, and a motor connected to said arm turning means to drive the latter.

3. The improvement breast pump assembly of claim 2 wherein said arm turning means and said motor operate at a suction stroke rate of about 50-60 cycles/min. and move the piston through a distance sufficient to create a maximum suction in the piston chamber in a range of about 100 to about 250 mmHg.

4. The improved breast pump assembly of claim 2 wherein said means for releasable receiving and holding the piston rod on said first end of said arm is a U-shaped resilient gripping member carried on said first end which is sized smaller than the diameter of the piston rod, and within which the piston rod is received and gripped.

5. The improved breast pump assembly of claim 2 wherein the forward end of the piston cylinder is screw-threaded for releasable substantially airtight attachment to a match-threaded portion of the breast-hood, said means mounted on said casing for releasably receiving and holding the forward end of the piston cylinder comprising an adaptor having a cap portion which is match-threaded to the piston chamber forward end for substantially airtight attachment thereon, an air channel formed in the cap through which air passes into the piston chamber, an outlet to said air channel to which an air tube can be connected, and a post formed on said cap which is received in a post-hole formed in said casing.

6. The improved breast pump assembly of claim 5 wherein said adaptor further includes a flange extending laterally from a side of said cap, said casing further including a slot formed therein adjacent said post-hole within which slot said flange is rotatably received to releasably fix said adaptor in place on said casing.

7. An adaptor for releasably mounting to a casing the forward end of a piston cylinder which is screw-threaded for releasable attachment to a match-threaded portion of a hand-drivable piston pump which is releasably attached to a breat-hood assembly of a hand-held manually operable breast pump, said adaptor comprising:

a cap portion which is match-threaded to the piston cylinder forward end for substantially airtight attachment thereon, an air channel formed in the cap through which air passes into the piston chamber of the piston cylinder, an outlet to said air channel to which an air tube can be connected, and a post formed on said cap which is receivable in a post-hole on the casing.

8. The adaptor of claim 7 wherein said adaptor further includes a flange extending laterally from a side of said cap, said flange being rotatably receivable in a slot formed in the casing adjacent the post-hole to releasably fix said adaptor in place on the casing.

9. A motor drive unit adapted to drive a breast pump assembly, wherein the breast pump assembly includes a hand-held manually operable breast pump having a hand-drivable piston pump with a piston received for reciprocating movement within a chamber of a piston cylinder to generate, in use, a periodic suction within a breast-hood emplaced on a breast to effect the expression of mother's milk, the piston cylinder having a forward end and a rearward end, the forward end being connectable to a breast-hood assembly including the breast-hood to generate suction in the breast-hood through movement of the piston in the piston cylinder, the piston having a piston rod connected thereto which is specifically adapted to be grasped to drive the piston, which piston rod extends out of the rearward end of the piston cylinder, wherein said motor drive unit comprises:

a casing, means for releasably receiving and holding the piston pump on said casing with the piston pump removed from the breast-hood, an air tube interconnecting the piston chamber with the breast-hood, and means for driving the piston rod for reciprocating movement in the piston chamber.

10. The motor drive unit of claim 9 wherein said arm turning means and said motor operate at a suction stroke rate of about 50-60 cycles/min. and move the piston through a distance sufficient to create a maximum suction in the piston chamber in a range of about 100 to about 250 mmHg.

11. The motor drive unit of claim 10 wherein said piston rod driving means includes a rotating eccentric cam having a camming surface which drives a first lever arm which is connected to a second lever arm having means thereon to hold the piston rod, said camming surface with said first and second arms producing an optimum stroke cycle as shown in FIG. 7.

12. A motor drive unit adapted to drive a breast pump assembly, wherein the breast pump assembly includes a hand-held manually operable breast pump having a hand-drivable piston received for reciprocating movement within a chamber of a piston cylinder to generate, in use, a periodic suction within a breast-hood emplaced on a breast to effect the expression of mother's milk, the piston cylinder having a forward end and a rearward end, the forward end being screw-threaded for connection to a breast-hood assembly including the breast-hood to generate suction in the breast-hood through rearward movement of the piston in the piston cylinder, the piston having a piston rod connected thereto which is specifically adapted to be grasped to drive the piston, which piston rod extends out of the rearward end of the piston cylinder, wherein said motor drive unit comprises:

a casing, an adaptor having a cap portion which is match-threaded to the piston cylinder forward end for attachment thereon, an air channel being formed in the cap through which air passes into the piston chamber with an outlet to said air chamber to which an air tube can be connected, and a post formed on said cap which is received in a post-hole formed in said casing, an air tube connectable with said outlet and the breast hood, an arm having first and second ends, said first arm end having means for releasably receiving and holding the piston rod, said second arm end being pivotally attached to said casing and connected to means for turning said arm through an arc in a reciprocating fashion to effect reciprocating movement of the piston rod to drive the piston, and a motor connected to said arm turning means to drive the latter.

13. The motor drive unit of claim 12 wherein said arm turning means includes a rotating eccentric cam having a camming surface which drives a lever arm which is connected to said arm having means for holding the piston rod, said camming surface, with said arms, producing an optimum stroke cycle as shown in FIG. 7.

* * * * *